(12) United States Patent
Pandya et al.

(10) Patent No.: US 7,840,512 B2
(45) Date of Patent: *Nov. 23, 2010

(54) MEDICAL ONTOLOGIES FOR COMPUTER ASSISTED CLINICAL DECISION SUPPORT

(75) Inventors: Abhinay Mahesh Pandya, Ahmedabad (IN); Romer E. Rosales, Downingtown, PA (US); R. Bharat Rao, Berwyn, PA (US); Harald Steck, Phoenixville, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/620,353

(22) Filed: Nov. 17, 2009

(65) Prior Publication Data

US 2010/0131438 A1   May 27, 2010

Related U.S. Application Data

(63) Continuation of application No. 11/505,080, filed on Aug. 16, 2006, now Pat. No. 7,630,947.

(60) Provisional application No. 60/711,117, filed on Aug. 25, 2005.

(51) Int. Cl.
  *G06F 17/00* (2006.01)
  *G06N 5/02* (2006.01)
(52) U.S. Cl. ........................................... 706/45
(58) Field of Classification Search ............... 706/12
  See application file for complete search history.

(56) References Cited

U.S. PATENT DOCUMENTS 7,630,947 B2 * 12/2009 Pandya et al. ............ 706/45

* cited by examiner

*Primary Examiner*—Michael Holmes
(74) *Attorney, Agent, or Firm*—Joshua Ryan

(57) ABSTRACT

Medical ontology information is used for mining and/or probabilistic modeling. A domain knowledge base may be automatically or semi-automatically created by a processor from a medical ontology. The domain knowledge base, such as a list of disease associated terms, is used to mine for corresponding information from a medical record. The relationship of different terms with respect to a disease may be used to train a probabilistic model. Probabilities of a disease or chance of indicating the disease are determined based on the terms from a medical ontology. This probabilistic reasoning is learned with a machine from ontology information and a training data set.

33 Claims, 2 Drawing Sheets

MEDICAL ONTOLOGIES FOR COMPUTER ASSISTED CLINICAL DECISION SUPPORT

RELATED APPLICATIONS

The present patent document is a continuation of U.S. patent application Ser. No. 11/505,080, filed Aug. 16, 2006, which claims the benefit of the filing date under 35 U.S.C. §119(e) of Provisional U.S. Patent Application Ser. No. 60/711,117, filed Aug. 25, 2005, the disclosures of which are hereby incorporated by reference.

BACKGROUND

The present embodiments relate to computer assisted clinical decision support. In particular, computer assisted medical decision support incorporates a medical ontology.

Medical ontologies provide information associated with one or more diseases and numerous medically relevant concepts (e.g., laboratory and diagnostic procedures; physiologic, biologic, genetic, molecular functions; organs and body parts; diseases, symptoms, and medical findings; etc). Different relationships between concepts are reflected by the medical ontology. For example, different names for a same disease are provided in an "IS A" type relationship. Related morphologies (e.g., inflammation) and body location are other types of relationships in the medical ontology. Medical ontologies may also contain various terms associated to a medical concept representing the same (or similar) meaning for the concept.

Medical ontologies provide information for computer assisted medical decision support. Computer assisted medical decision support systems may be deterministic. For example, a rule-based system alerts clinicians to drug-drug interaction. The rules are determined manually from the medical ontology.

Rule-based systems may support only a fraction of medical decisions. Rule-based systems typically require structured input (e.g., billing, demographic, lab, pharmacy or other rigidly formatted or input information). However, medical information used in medical decisions may be in an unstructured format (e.g., text, physician notes, or images). Rule-based systems may have incomplete information.

Medical decision-making is frequently probabilistic, so a deterministic, rule-based system may not adequately support such decisions. Simplistic combinations of multiple "IS A" type relationships input to the system indicating a greater chance of having the disease have been used. For example, a greater number of terms with an "IS A" relationship indicates a greater chance of having a disease. However, this simple approach may not accurately reflect probabilities.

More complex probabilistic inference systems have been used for medical decision support. Such systems are often hard to build, requiring finely tuned domain knowledge coded by hand. These systems are built on a network of concepts elicited, painstakingly, from physicians. Further, these systems require precise probabilities to be set, but such probabilities are hard to find. Physicians implicitly perform probabilistic inference very well in day-to-day work, but find it very hard to set precise numerical probabilities when asked. Once created, these systems are hard to maintain. As medical knowledge changes, the systems are changed. Making additions or deletions to such systems is difficult due to the need to identify the differences and again assign probabilities. These systems also work off structured patient data.

BRIEF SUMMARY

By way of introduction, the preferred embodiments described below include methods, systems, and instructions for use of a medical ontology for computer assisted clinical decision support. Medical ontology information is used for mining and/or probabilistic modeling. A domain knowledge base may be automatically or semi-automatically created by a processor from a medical ontology. The domain knowledge base, such as a list of disease-associated terms or other medical concepts or terms, is used to mine for corresponding information from a medical record. The relationship of different terms with respect to a disease or concept may be used to train a probabilistic model. A probability of disease or a chance of a term indicating the disease or concept is determined based on the terms from a medical ontology. This probabilistic reasoning is learned with a machine from ontology information and a training data set.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A probabilistic decision-support system is formed from a medical ontology. The probabilistic decision-support system may operate independently of or be incorporated into a data mining system. Existing or future medical ontologies, such as MeSH and UMLS, provide relationship information for various terms. For instance, the ontologies provide a hierarchy of concepts wherein general concepts appear higher in the ontology—"is a" ontologies wherein each child "is a" more specific instance of its parent (e.g., for example, "Heart Failure" is a kind of "Cardiovascular disease"). Ontologies also contain additional information about morphology, symptoms, associated drugs, side effects, causes, or other relationships. All or some of this information enriches the probabilistic decision-support system, for instance, by semi or automatically building the probabilistic network. Probability values are assigned to the terms from the medical ontology. Once the term structure is defined, a large pool of patient cases is used to learn these probabilities. The learning may be automatic with no manual input, or semi-automatic with user tuning or minimal manual input.

A medical ontology may be used for data mining. Natural language processing or other data mining engines use the medical ontology information. To create a mining engine for a specific disease, condition, symptom, cause, other concept, or other information, the medical ontology is analyzed by a processor. The associated terms are selected and incorporated into a domain-knowledge base. The mining is performed based on the medical ontology terms in the domain knowledge base. The extracted features can then be used by the decision-support system. The medical ontology may also indicate which features are the most important to extract, providing for selection of different terms. The mined information may be used to infer medical conditions from unstructured data (e.g., textual) and/or structured evidence. Additionally or alternatively, the mining may infer data based on probabilities determined using medical ontology information.

Using a medical ontology in a decision support system may improve the accuracy of the learnt graphical model, decrease the time complexity of learning, and/or more thoroughly determine appropriate information to use in a model or mining.

Figure 1:
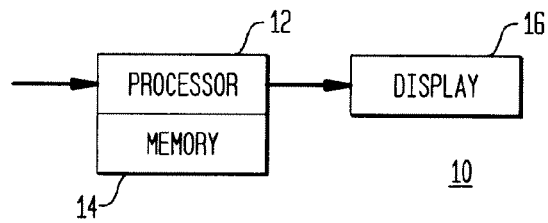
FIG. 1 is a block diagram of one embodiment of a system for use of a medical ontology for computer assisted clinical decision support.

FIG. 1 shows a system 10 for use of a medical ontology for computer assisted clinical decision support. The system 10 includes a processor 12, a memory 14 and a display 16. Additional, different or fewer components may be provided. The system 10 is a personal computer, workstation, medical diagnostic imaging system, network, or other now known or later developed system for providing decision support. For example, the system is a workstation for analyzing a medical ontology, training a probabilistic model, or generating domain knowledge. As another example, the system 10 is a computer aided diagnosis system incorporating information from a medical ontology. Automated assistance is provided to a physician for classifying a state appropriate for given medical information, such as the records of a patient. Assistance is provided for diagnosis of heart diseases, breast cancer, lung cancer, other disease, symptoms, causes, effects or other medically useful information. The automated assistance is provided after subscription to a third party service, purchase of the system 10, purchase of software or payment of a usage fee.

The processor 12 is a general processor, digital signal processor, application specific integrated circuit, field programmable gate array, analog circuit, digital circuit, combinations thereof or other now known or later developed processor. The processor 12 may be a single device or a combination of devices, such as associated with a network or distributed processing. Any of various processing strategies may be used, such as multi-processing, multi-tasking, parallel processing or the like. The processor 12 is responsive to instructions stored as part of software, hardware, integrated circuits, film-ware, micro-code or the like.

The processor 12 operates to create from medical ontologies and/or to apply a knowledge base or trained model based on medical ontologies. Medical ontologies include MeSH, UMLC, and Snomed CT. Other now existing or later developed medical ontologies may be used.

For creating, the processor 12 analyzes one or more medical ontologies. One ontology may be used for one type of information, such as symptoms, and another ontology used for another type of information, such as "IS A" relationships. One ontology may be used for one disease, and another ontology may be used for another disease. A plurality of ontologies may be used for the same disease and/or types of relationships. In the examples herein, the ontologies are used for disease specific decision support, but the ontologies may be used for symptom, cause, effect, signs, other concepts, or other features for analysis.

Figure 3:
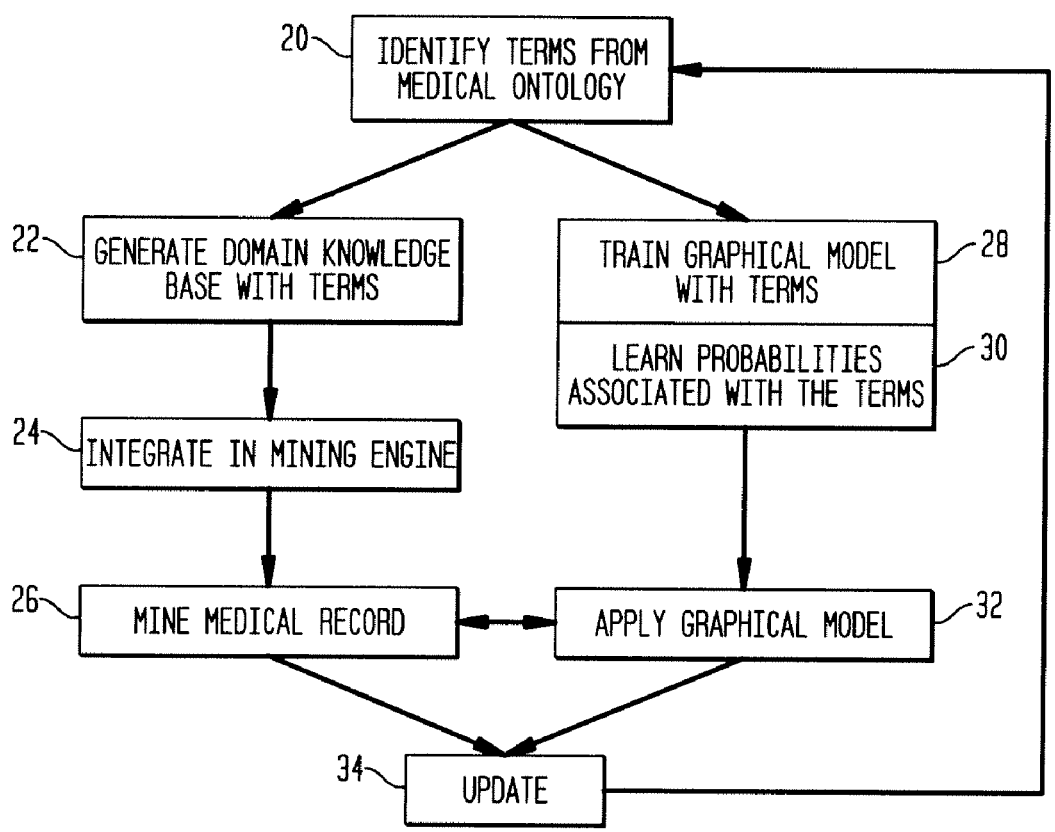
FIG. 3 is a flow chart diagram showing one embodiment of a method for use of a medical ontology for computer assisted clinical decision support.

The processor 12 analyzes the ontology by searching for terms with specific relationships. Medical ontologies are provided in a structured format, with different links between different terms. FIG. 3 shows an example ontology for appendicitis. Direct or "IS A" type relationships are indicated graphically as being in a same vertical column, but may be linked electronically in any manner. Site or body location relationships are indicated by a different link, such as a finding site link. Morphology relationships are indicated by another different link, such as an associated morphology link. Other relationships may include a cause, an effect, a symptom, a sign, drugs, tests, or a related disease. For example, diabetes may be shown as related to or connected with heart failure, but is not the same or an "IS A" relation. Diabetes may be related since a person with diabetes is more likely to have heart failure than a person without diabetes.

The processor 12 searches for a disease or other term of interest. Once located in the ontology, the terms from the desired relationships are also identified. The type of relationship, distance (e.g., number of intervening terms), direction of link, or other restriction may be used to determine associated terms. For example, terms from one, two, three or more different types of relationships are extracted. Alternatively, all direct and/or indirect links to the term of interest are identified. The relationships of the terms may also be identified. As an alternative to processor 12 searching, a user manually identifies terms and creates a list.

The associated terms are collected. The collection may be examined manually, such as by a physician confirming desired results. The collection may be used automatically in a leave one out approach to identify desired results, such as selecting only terms associated with a sufficient probability based on later training. The collection may be limited in response to user input during extraction or use, such as the user selecting relationship types or distance parameters. Alternatively, the collection is used without further restriction.

For data mining, such as natural language processing, the processor 12 generates a domain knowledge base from associated terms. The terms included depend on the domain, such as using only terms associated with a specific disease. The domain knowledge base is a list of the associated terms. The terms may be truncated (e.g., "inflammation" truncated to "inflam*") or otherwise altered to generate the knowledge base.

For diagnosis support, a graphical or probabilistic model is built from the associated terms and/or relationship information. For example, a Bayesian network, a conditional random field, an undirected network, a hidden Markov model and/or a Markov random field is trained by the processor 12. The model is a vector with a plurality of variables, but other model representations may be used. Single level or hierarchal models may be used. For training, both training data and ontologies information are combined. Formal criteria and/or algorithms may be incorporated. By using ontologies, the built probabilistic model may better represent the underlying relationship between concepts or entities. No or more limited manual expert intervention may be required to build the probabilistic model. For example, an expert may assist in tuning the probabilistic model after or while being built. As another example, the expert may merely indicate the actual disease state associated with the medical records of the training data.

The processor 12 is operable to apply a mining engine to a medical record. The mining engine uses the domain knowledge base extracted from the medical ontology. For example, a variable is assigned to each of the associated terms from the knowledge base. The mining engine searches for the associated terms in structured and/or unstructured portions of the medical record. In one embodiment, the mining engine is part of the REMIND (Reliable Extraction and Meaningful Inference from Non-structured Data) system, such as described in U.S. Publication Nos. 2003/0120458, 2003/0120133, 2003/0120134, 2003/0126101 or 2003/0130871, which are incorporated herein by reference. REMIND is a Bayesian framework that integrates and blends structured and unstructured clinical data in patient records to automatically create structured clinical data as an output. This structuring allows existing patient records to be mined for quality assurance, regulatory compliance, diagnosis assistance, and to relate financial and clinical factors. The mining engine may output any matching terms.

The mining engine may further infer a patient state as a function of the matched associated terms and corresponding probabilities of the associated terms indicating the patient state. The processor 12 applies the probabilistic model generated, in part, from the ontology information. The results of the data mining are applied as inputs to the probabilistic model. The patient state, such as the existence of a disease, or other information is inferred based on probabilities determined by training with ontology information. In alternative embodiments, the probabilistic model is applied without the data mining, such as using manual input, or without mining unstructured data, such as using a structured input data set acquired without data mining based on ontology information.

The memory 14 is a computer readable storage media. Computer readable storage media include various types of volatile and non-volatile storage media, including but not limited to random access memory, read-only memory, programmable read-only memory, electrically programmable read-only memory, electrically erasable read-only memory, flash memory, magnetic tape or disk, optical media and the like. The memory 14 may be a single device or a combination of devices. The memory 14 may be adjacent to, part of, networked with and/or remote from the processor 12.

The memory 14 may store the medical ontology. For example, a spreadsheet of the ontology terms and relationships is stored. The medical ontology may be scanned and/or OCRd for storage into the memory. Alternatively, the memory 14 stores information extracted from the medical ontology, such as associated terms, relationships, domain knowledge or combinations thereof.

The memory 14 may store training data. The training data is a collection of two or more previously acquired patient records and corresponding labels or ground truths. For example, hundreds, thousands or tens of thousands of patient records are obtained and stored. In one embodiment, the records are originally created as part of a clinical study. In other embodiments, the records are gathered independent of a clinical study, such as being collected from one or more hospitals.

Each training set includes extracted variables for a plurality of features. The different patient records have the same extracted features, but one or more patient records may have fewer or a greater number of features. Alternatively, one or more of the patient records includes information to be used for extracting features, such as including an image. Any format may be used for maintaining and storing the training data.

The memory 14 may store a patient record. The patient record is input manually by the user and/or determined automatically. The patient record may be formatted or unformatted. The patient record resides in or is extracted from different sources or a single source. The patient record includes variables available for a current patient. The variables correspond to features, such as medical history, pain indication, lump indication, age, genetic information, test results, family history, billing codes, medications, lab results, notes, text, or other sources of information. The patient record may include one or more images of a same or different type. The processor 12, a different processor or the user may extract variables from the image. The variables correspond to features of the image. Any now known or later developed patient record format, features and/or technique to extract features may be used.

The memory 14 may store a mining engine. The mining engine includes the domain-knowledge base created from associated terms of a medical ontology. The mining engine is software, code or other instructions for mining one or more patient records. The mining engine is operable to mine the medical record as a function of the domain-knowledge base. The mining engine searches in structured and/or unstructured data of the medical record. The mining engine searches for the associated terms from the medical ontology.

The memory 14 may store a probabilistic or other graphic model having machine-learned probabilities derived, in part, from a medical ontology. The associated terms represent different relationships, such as terms associated through cause, effect, a different disease or combinations thereof for a disease. For each term or relationship between two terms, a probability is provided. The probabilities may be combined based on identified or input terms for a given patient to probabilistically reason a chance the patient has the disease.

More than one classifier or model may be stored, such as having different models for different combinations of available data. Alternatively, the model allows for missing information. Each model is stored as a matrix, but more complex classifier algorithms, instruction sets, logic, or tools may alternatively or additionally be stored.

The memory 14 may be a computer readable storage media having stored therein data representing instructions executable by the programmed processor 12 for use of a medical ontology for computer assisted clinical decision support. The memory 14 stores instructions for the processor 12. The processor 12 is programmed with and executes the instructions. The functions, acts, methods or tasks illustrated in the figures or described herein are performed by the programmed processor 12 executing the instructions stored in the memory 14. The functions, acts, methods or tasks are independent of the particular type of instructions set, storage media, processor or processing strategy and may be performed by software, hardware, integrated circuits, film-ware, micro-code and the like, operating alone or in combination.

The instructions are for extracting associated terms from a medical ontology, for creating or applying a domain knowledge base, and/or for training or applying a probabilistic model as a function of extracted terms from a medical ontology. In one embodiment, the instructions are stored on a removable media drive for reading by a medical diagnostic imaging system or a workstation. An imaging system or workstation uploads the instructions. In another embodiment, the instructions are stored in a remote location for transfer through a computer network or over telephone lines to the imaging system or workstation. In other embodiments, the instructions are stored within the imaging or system on a hard drive, random access memory, cache memory, buffer, removable media or other device.

The instructions may cause the processor 12 to create a knowledge base from a medical ontology. A plurality of associated terms is identified from the medical ontology, and the knowledge base is generated from the associated terms. In an additional or alternative embodiment, the instructions cause the processor 12 to build a mining engine operable to search unstructured medical data as a function of terms from the medical ontology, such as from the knowledge base.

The instructions may cause the processor 12 to apply a mining engine built as a function of information from a medical ontology. A medical record is mined as a function of a knowledge base derived from the medical ontology. Medical data, such as the patient record or portions of the patient record, is input to the processor 12 or the memory 14. The medical data is from one or more sources of patient information. For example, one or more medical images are input from ultrasound, MRI, nuclear medicine, x-ray, computer thermography, angiography, and/or other now known or later developed imaging modality. Additionally or alternatively, non-image medical data is input, such as clinical data collected over the course of a patient's treatment, patient history, family history, demographic information, billing code information, symptoms, age, genetics or other indicators of likelihood related to the abnormality or disease detection being performed. For example, whether a patient is female, has a history of breast cancer problems, has a detectable lump, has pain, has a family history of breast cancer or is old may indicate a likelihood of breast cancer. Other features may be used for breast cancer determination. The same and/or different features may be used for assisted diagnosis of other diseases.

The information is extracted automatically, such as described in U.S. Publication Nos. 2003/0120458, 2003/0120133, 2003/0120134, 2003/0126101 or 2003/0130871, which are incorporated herein by reference. Information is automatically extracted from patient data records, such as both structured and unstructured records. Probability analysis may be performed as part of the extraction for verifying or eliminating any inconsistencies or errors. The system may automatically extract the information to provide some missing data. The processor 12 performs the extraction of information. Alternatively, other processors perform the extraction and input results, conclusions, probabilities or other data to the processor 12. Other automated extraction or importing of a patient record may be used, such as instructions for a routine to import patient record information from a structured database or mining without probability based inference.

The instructions may cause the processor 12 to create a graphical or probabilistic model. For example, associated terms and relationships from a medical ontology are correlated with training data and associated truths to train a graphical model. After machine learning, a matrix or other model provides probabilistic reasoning for the existence or lack of a condition, such as a disease.

The instructions may cause the processor 12 to apply a graphical or probabilistic model trained as a function of information from a medical ontology. The model is applied to a medical record for one or more patients. The inputs for the model are determined from the medical record, such as by an output of mining or manual input. For example, the instructions control a user interface to solicit entry of information manually by an operator.

The graphical or probabilistic model is used for mining, diagnosis or other purpose. For example, the mining infers proper data to fill in missing information or resolve inconsistencies based on probabilities learnt using machine learning from ontology information. As another example, the graphical or probabilistic model is applied to determine, from the medical record, a chance of a disease. The probabilities are machine learnt based on "IS A" and/or other relationships from a medical ontology.

The display 16 is a CRT, monitor, flat panel, LCD, projector, printer or other now known or later developed display device for outputting determined information. For example, the processor 12 causes the display 16 at a local or remote location to output data indicating mining results, a possible diagnosis, a probability associated with one or more possible diagnoses, an image with marked locations of interest, medical record information supporting a probability or inference, or other medical decision assistance associated with the current patient record. The output may be stored with or separate from the patient record.

FIG. 3 shows a method for use of a medical ontology for computer assisted clinical decision support. The method is implemented using the system 10 of FIG. 1 or a different system. Additional, different or fewer acts than shown in FIG. 3 may be provided. For example, act 34 may not be performed. As another example, only acts 20 and 22, 26, 28 or 32 are performed. The acts are performed in the order shown or a different order. The acts may be performed automatically, manually, or combinations thereof.

In act 20, a plurality of associated terms is identified from a medical ontology. A processor performs the identification, but the terms may be manually identified. The terms are identified from one or more ontologies. The associated terms may have different relationships with a term of interest, such as identifying the associated terms as having a IS-A type, cause, effect, symptom, sign, related disease, body location, drug, and/or morphology relationship. A plurality of terms of interest may be used. For example, two or more sets of terms associated with different terms of interest are identified. Overlapping terms are selected to form a set of desired associated terms. Each term of interest may be any type of data, such as disease, a morphology or a term from any of the other relationship types described herein.

Figure 2:
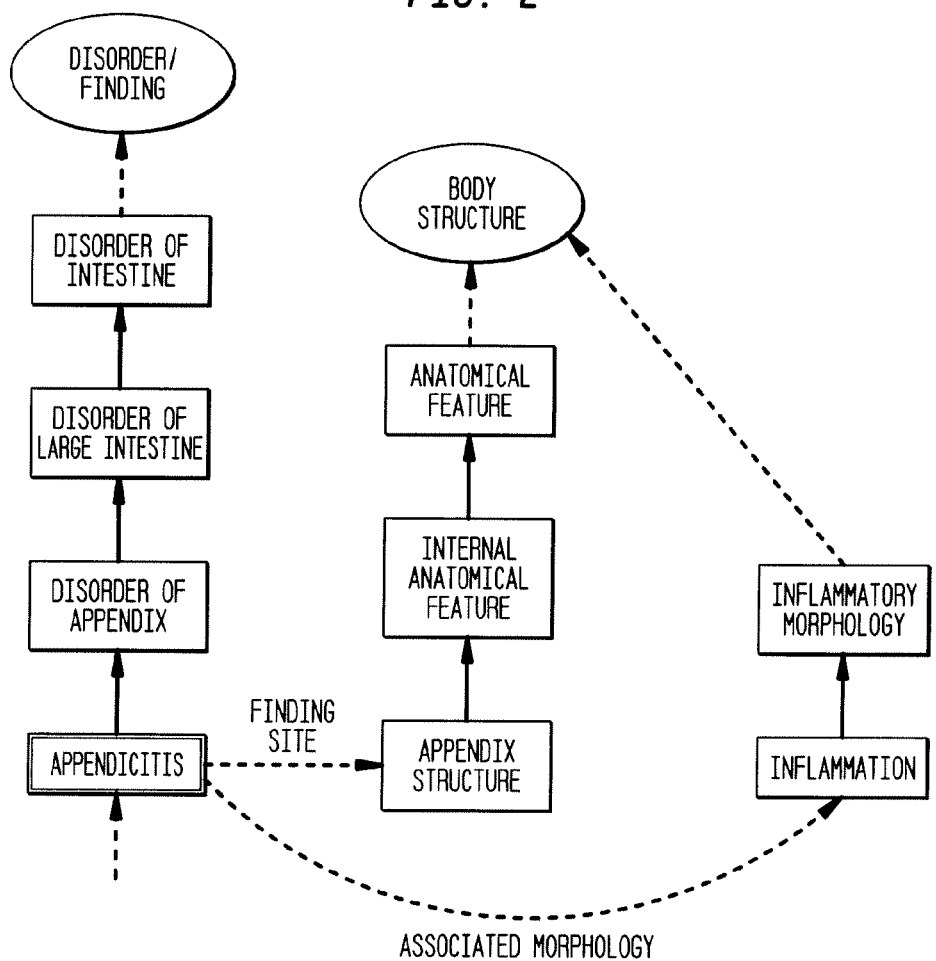
FIG. 2 is a graphical representation of a portion of a medical ontology.

In one embodiment, given some concept or term of interest, all the sub-concepts consistent with the ontology are identified. It is assumed that sub-concepts always imply the broader concept so that the concepts may be inferred from the sub-concepts. A concept is a term of interest and a sub-concept is related by an "IS A" relationship. For example, a concept is heart failure. Sub-concepts may be cardio vascular disease, myopathy or other more generic or more specific terms indicating heart failure. When the relationships are not of this concept, sub-concept type (i.e., IS-A type), the implication of probability is not necessarily deterministic or guaranteed. The relationship strength about the related entities may also be uncertain. An example of this other type of relationship is shown in FIG. 2. The concept "appendicitis" in the finding/disorder hierarchy in SNOMED is the term of interest. The attributes associated morphology, and finding site connects this concept to Inflammation and Appendix structure concepts of Body structure hierarchy respectively as non-IS A relationships. These terms may also be identified for possible use in mining and/or diagnosis.

The ontology represents one or various types of relationships between concepts, including IS-A type. The concept of interest is identified in the ontology by searching. Sub-concepts (i.e., through IS-A type relationships) are identified in the ontology. Concepts related to the above concepts through other relationship types are identified in the ontology. The resulting group of concepts and sub-concepts are associated terms.

The identification of associated terms may be restricted. For example, the distance in the medical ontology between the concept of interest and the current term is limited. In FIG. 2, the distance may be limited to any number of links, such as two. The term "disorder of the intestine" or "anatomical feature" is not included. The limit may be different for different types of relationships, such as three for IS A (e.g., include "disorder of the intestine") and only two for finding site (e.g., include "appendix structure" and "internal anatomical feature," but not include "anatomical feature"). Other limitations may be alternatively or additionally provided, such as limiting the types of association or relationships.

In act 22, the processor or user generates a domain knowledge base form the associated terms. For example, a variable is assigned to each of the associated terms. Each identified concept or sub-concept is assigned a random variable in the graphical model or domain knowledge base.

In act 24, the domain knowledge base is integrated into a mining engine. For example, a pointer to a storage location or file name of the domain knowledge base is incorporated into the mining engine, or the knowledge base is stored with a specific name for calling by the mining engine. Alternatively, the mining engine incorporates the knowledge base as part of the programming or code of the mining engine. The mining engine is operable as a function of the information from the medical ontology.

In act 26, a medical record is mined as a function of the domain-knowledge base. The mining is a function of the information from the medical ontology. The mining engine searches for the associated terms or derivatives of the associated terms from the knowledge base for the disease or information of interest.

Data for a current patient record or records is obtained. For example, the medical data is obtained automatically, through user input or a combination thereof for a particular patient being examined. The medical data is structured or unstructured. The mining engine is an information extraction system that identifies occurrences of medical concepts or sub-concepts. The medical concepts or sub concepts described by MeSH, SNOMED CT, or other medical ontologies are located in electronic medical records. For example, terms that appear or are mentioned in the text records (e.g., doctor's notes) are located.

The mining is free of probability determination. Alternatively, probabilistic reasoning is used for the data mining. For example, probabilities associated with different terms are examined to resolve missing data or inconsistent date situations. As another example, a patient state is inferred as a function of the associated terms and corresponding probabilities of the associated terms indicating the patient state as discussed below in act 32. The probabilities may be manually provided or trained with machine learning techniques as discussed below in act 30.

In act 28, a graphical model is trained. A processor trains the graphical model for probabilistic reasoning. The associated terms from the medical ontology are applied to a training data set. The model is built automatically by employing both training data (structured and/or unstructured), such as a collection of electronic medical records in a database, and ontologies (e.g., the Unified Medical Language System), a representation that captures relationships that hold among the records or attributes in the database.

Probabilities of the associated terms are determined by machine learning. Graphical models are built from ontologies where probabilistic relationships are represented by the probability distribution implied by the model. A probability distribution over the state-space of individual concepts/entities (e.g., a binary state-space) is computed. The model is built by optimizing a function of both the training data and the associated terms from, the ontology. The relationships are calculated by observing sample data but also by automatically incorporating knowledge encoded in the ontologies, reducing the need for manual expert intervention.

In one embodiment, a variable in the graphical model is assigned to each associated term. Each data point is represented as a random vector of as many dimensions as variables in the graphical model, one dimension or scalar variable entry per variable. In each vector, the entries or values for the variables can be missing or observed. The training data is constructed or treated as a plurality of vectors, each vector having a location for each of the variables. A disease of interest corresponding to the associated terms is labeled. The entry corresponding to the concept of interest is labeled according to associated sub-concepts or terms. The labeling depends on the application of interest.

The graphical model is trained in act 28 from the training data as represented above (i.e., with the vectors). The graphical model may be trained even where at least one variable of at least one vector has a missing value. Any process may be used. The graphical model is built with a single pass, or an iterative process is provided. Different combinations of some or all of the available variables from the selected set are tried. Different types of models or combinations of models may be attempted. The best performing one or ones are assigned. Alternatively, a first sufficiently performing classifier is assigned and no further classifiers are built. In other embodiments, the different combinations or iterations are guided logically or based on a knowledge base. Any possible tuning may be provided, such as automated tuning and/or manual tuning based on information in the training data. The model may be applied to the training data for tuning.

In act 30, probabilities are learnt by training. The probability is of a given term or variable to indicate a likelihood of a patient state. The probability may be determined alone or in conjunction with one or more combinations of other variables, such as determining a probability associated with a combination of terms. All or only some of the associated terms from the medical ontology may be used. For example, the processor selects variables from the training set. The training set may not include the current patient record. Automated variable selection may be based on machine-learnt processes for variable selection and/or programmed identification. A leave one out approach may be used to identify variables associated with sufficient probability. Alternatively, manual input assists in selection of variables.

The resulting probabilistic model characterizes the relationship between a set of variables representing concepts, sub-concepts, associated terms or entities of interest in a given domain. In act 32, the graphical or probabilistic model is applied to a current medical record. For example, medical record information is input in any manner to the graphical model. The graphical model outputs a suggested diagnosis based on the learned relationships and corresponding probabilities for the terms from the ontology. A probability corresponding to the associated diagnosis may be provided. The diagnosis and the probability are determined by learned probabilistic reasoning. The model may be operable even where some variables or values for the current medical record are not input. Alternatively, the variables or values are inferred.

The model may be applied in act 32 with or part of applying data mining in act 26. For example, the outputs of the data mining are input to the graphical model. The model allows definition of the posterior probability mass function for a variable of interest, given observed evidence or information. The resulting diagnosis is a function of the domain-knowledge base from the medical ontology, the probabilities determined for terms from the medical ontology, and training data. As another example, the built model can be used to perform inferences about unobserved concepts (represented as variables) from unstructured (e.g., text) and structured data.

In an alternative embodiment, a patient state is determined without a trained system. For example, a set of associated terms is identified. The patient state is determined as diseased if the current medical record includes the terms, a threshold number of the terms, or particular combinations of terms. The threshold or combinations to be used may be selected manually or based on machine-learnt probabilities.

In act 34, the domain knowledge base, graphical model or other information is updated based on new or different medical ontology information. For example, an additional ontology is provided, or a previously used medical ontology is altered. An update of the medical ontology is received by the processor. One or more of the other acts 20-32 are preformed based on the updated information. For example, the process is repeated to recreate the domain knowledge or graphical model. Alternatively, the differences are determined and the new information is used to update the knowledge base or graphical model. Since the process is semi or fully automatic, updates may be less burdensome than maintaining and updating a manual expert based system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for use of a medical ontology for computer assisted clinical decision support, the method comprising:
   identifying, with a processor, a plurality of associated terms from a medical ontology, the associated terms including associated drugs;
   generating, with the processor, a domain-knowledge base from the associated terms, including the associated drugs; and
   mining a medical record as a function of the domain-knowledge base, the mining including mining for the associated drugs.

2. The method of claim 1 wherein identifying comprises identifying the associated terms as having a IS-A type relationship from the medical ontology.

3. The method of claim 1 wherein identifying comprises identifying at least some of the associated terms as causes, effects, symptoms, signs, related diseases, body locations, morphology, laboratory procedures, diagnostic procedures, physiologic information, biologic information, genetic information, molecular functions, organs, body parts, medical findings, side effects, tests, or combinations thereof of a disease.

4. The method of claim 1 wherein identifying comprises identifying at least some of the associated terms of a clinical concept, the clinical concept other than a disease.

5. The method of claim 1 wherein identifying comprises identifying the associated terms from the medical ontology and an additional medical ontology.

6. The method of claim 1 wherein generating comprises assigning a variable to each of the associated terms.

7. The method of claim 1 further comprising:
   restricting the identification of associated terms as a function of distance in the medical ontology, type of association, or combinations thereof.

8. The method of claim 1 wherein mining the medical record comprises searching for the associated term or terms in structured and unstructured portions of the medical record.

9. The method of claim 1 wherein mining the medical record comprises inferring patient states for multiple patients, the inferring being as a function of the associated terms and corresponding probabilities of the associated terms indicating the patient states.

10. The method of claim 1 further comprising:
    training, with the processor, a graphical model as a function of the domain-knowledge base and training data.

11. The method of claim 1 further comprising:
    receiving an update of the medical ontology; and
    repeating the identifying and generating for the update.

12. A system for use of a medical ontology for computer assisted clinical decision support, the system comprising:
    a memory operable to store a mining engine with a domain-knowledge base from associated terms in a medical ontology, the mining engine configured to mine a medical record as a function of the domain-knowledge base; and
    a processor configured to apply the mining engine to the medical record, the processor associated with a network or distributed processing.

13. The system of claim 12 wherein the associated terms from the medical ontology are from three or more of the groups of: having a IS-A type relationship, a cause, an effect, a symptom, a sign, a related disease, a body location, laboratory procedures, diagnostic procedures, physiologic information, biologic information, genetic information, molecular functions, organs, body parts, medical findings, side effects, tests, and morphology.

14. The system of claim 12 wherein a variable is assigned to each of the associated terms, and wherein the mining engine is operable to search for the associated terms in structured and unstructured portions of the medical record and infer a patient state as a function of the associated terms and corresponding probabilities of the associated terms indicating the patient state.

15. In a computer readable storage media having stored therein data representing instructions executable by a programmed processor for use of a medical ontology for computer assisted clinical decision support, the storage media comprising instructions for:
    creating a knowledge base from a medical ontology; and
    building a mining engine operable to search unstructured medical data as a function of the knowledge base, the mining engine operable to search for terms in the knowledge base and output matches for quality assurance, regulatory compliance, diagnosis assistance, or relation of financial and clinical factors.

16. The instructions of claim 15 wherein creating the knowledge base comprises identifying a plurality of the terms from the medical ontology and generating the knowledge base from the terms.

17. A method for use of a medical ontology for computer assisted clinical decision support, the method comprising:
    identifying a plurality of associated terms from a medical ontology; and training, with a processor, a model of relationships of the associated terms as a function of the associated terms and training data of medical records representing patients.

18. The method of claim 17 wherein identifying comprises identifying the associated terms as having a IS-A type relationship from the medical ontology.

19. The method of claim 17 wherein identifying comprises identifying at least some of the associated terms as causes, effects, symptoms, signs, related diseases, body locations, laboratory procedures, diagnostic procedures, physiologic information, biologic information, genetic information, molecular functions, organs, body parts, medical findings, side effects, tests, morphology, or combinations thereof of a disease.

20. The method of claim 17 wherein training comprises assigning a variable in the graphical model to each associated term.

21. The method of claim 20 wherein training comprises constructing the training data as a plurality of vectors, each vector having a location for each of the variables, labeling a disease of interest corresponding to the associated terms, and training the model from the training data where at least one variable of at least one vector has a missing value.

22. The method of claim 20 further comprising:
creating a knowledge base from a medical ontology;
wherein training comprises building a mining engine operable to search unstructured medical data as a function of the knowledge base.

23. A system for use of a medical ontology for computer assisted clinical decision support, the system comprising:
a memory operable to store a probabilistic model having machine learned probabilities for relationships from a medical ontology, the machine learned probabilities for the relationships learned from the medical ontology automatically with no manual input or semi-automatically with user tuning; and
a processor operable to apply the probabilistic model.

24. The system of claim 23 wherein the relationships from the medical ontology comprise cause, effect, or combinations thereof for a disease.

25. The system of claim 23 wherein the relationships from the medical ontology comprise a different disease relationship with a disease of interest.

26. The system of claim 23 wherein the processor is operable to mine unstructured data of a medical record as a function of a knowledge base derived from the medical ontology, and wherein the processor is operable to apply the probabilistic model to results of the mining.

27. A method for use of a medical ontology for computer assisted clinical decision support, the method comprising:
identifying, with a processor, a plurality of associated terms from a medical ontology;
generating, with the processor, a domain-knowledge base from the associated terms; and
mining a medical record as a function of the domain-knowledge base, the medical record comprising a medical image, non-image medical data, or combinations thereof.

28. The method of claim 27 wherein the medical record comprises the medical image, the medical image being from ultrasound, magnetic resonance, nuclear medicine, x-ray, or angiography.

29. The method of claim 27 wherein the medical record comprises the non-image medical data, the non-image medical data comprising clinical data collected over a course of patient treatment, patient history, family history, demographic information, billing code information, symptoms, age, or genetics.

30. A method for use of a medical ontology for computer assisted clinical decision support, the method comprising:
identifying a plurality of associated terms from a medical ontology;
generating, with a processor, a domain-knowledge base from the associated terms; and
mining, with a data mining system, a medical record of a patient, the mining being as a function of the domain-knowledge base.

31. The method of claim 30 wherein identifying comprises identifying from a user created list.

32. The method of claim 30 wherein identifying comprises identifying by a processor.

33. A method for use of a medical ontology for computer assisted clinical decision support, the method comprising:
identifying, with a processor, a plurality of associated terms from a medical ontology, wherein identifying comprises identifying at least some of the associated terms as causes, effects, symptoms, signs, related diseases, body locations, morphology, laboratory procedures, diagnostic procedures, physiologic information, biologic information, genetic information, molecular functions, organs, body parts, medical findings, side effects, tests, or combinations thereof of a disease;
generating, with the processor, a domain-knowledge base from the associated terms; and
mining a medical record as a function of the domain-knowledge base.

* * * * *